United States Patent [19]

Michel

[11] 4,167,559

[45] Sep. 11, 1979

[54] DEODORIZING BREATH COMPOSITION

[76] Inventor: George H. Michel, 343 Oak Knoll Dr., Glendora, Calif. 91740

[21] Appl. No.: 790,041

[22] Filed: Apr. 22, 1977

[51] Int. Cl.$^2$ .................. A61K 7/26; A61K 9/68; C07J 00/00

[52] U.S. Cl. ......................................... 424/58; 424/48

[58] Field of Search .................. 424/58, 48; 260/210.5

[56] References Cited

U.S. PATENT DOCUMENTS

| | | | |
|---|---|---|---|
| 877,401 | 7/1907 | Buchanan | 424/58 |
| 2,791,581 | 5/1957 | Wall et al. | 260/210.5 |

OTHER PUBLICATIONS

Chem. Abst., 6th Collective Index, 1957–1961.

*Primary Examiner*—Delbert R. Phillips
*Attorney, Agent, or Firm*—Boniard I. Brown

[57] ABSTRACT

A composition of natural food stuffs based mainly upon the extract of the Yucca plant and a protein is provided which acts as an oral cavity cleansing and breath deodorizing agent.

7 Claims, No Drawings

DEODORIZING BREATH COMPOSITION

BACKGROUND OF THE INVENTION

1. Field of the invention

This invention is related to the field of food stuffs in general and more particularly to food stuffs based on ingredients which cleanse the mouth and deodorize the breath.

2. Prior Art

There are numerous tablets, pills, liquids, sprays and chewing gums on the market which purport to function as breath refresheners. Typical examples of such products are: the Clorets, sold in the form of tablets and chewing gum, which are comprised of sugar, corn syrup, natural flavors, magnesium stearate, vegetable oil, and activated water soluble chlorophyll; the Certs tablet comprised of copper gluconate, magnesium stearate, vegetable oil, sugar and corn syrup; the Tic Tac pills comprised of sugar, dextrins, rice starch, corn syrup, natural flavors, artificial flavors, magnesium stearate and cadelill wax; and the Dynamint pills comprised of sugar, dextrins, starch, stearic acid, cadelill wax, natural and artificial flavorings.

While each of the prior art materials exhibit varying degrees of effectiveness in masking odors, none of the prior art compositions are effective in removing alcohol and tobacco odors from the oral cavity for prolonged time periods. The active ingredients of the prior art compositions are generally the sugars, artificial flavors and in some cases chlorophyll which merely mask the odors.

Applicant does not know of prior art compositions which utilize the particular active ingredients of the instant invention to function as a breath refreshener or deodorizer.

THE INVENTION

SUMMARY

In seeking to develop a composition, useful as a breath refresher, which effectively rids the oral cavity of alcoholic and tobacco odors while avoiding the disadvantages of prior art breath tablets, a composition composed of the natural extract from the Yucca plant and a protein as its active ingredients along with other natural materials as fillers and/or coloring agents has been discovered.

This composition is prepared with from 1 to 90% of the Yucca extract, and from 10 to 90% of the protein in tablet form by incorporating fillers, lubricants, binding agents, coloring agents and sweeteners.

From the teachings below, it can been seen that the principal objective of this invention is to provide an effective breath cleansing tablet.

A further objective of this invention is to provide a breath tablet comprised primarily of natural food stuffs.

A still further objective of this invention was to provide a breath tablet that has a pleasant taste.

A final objective of this invention is to provide a breath tablet comprised of materials which do not harm the body and still accomplish the principal objective.

DETAILED DESCRIPTION OF THE INVENTION

It has been discovered that the natural Yucca extract, obtained by steam treating the pulp of the Yucca plant with water, when combined with a protein exhibits a synergestic effect in eliminating odors from the breath and oral cavity of humans.

The cavity cleansing is accomplished by the absorptive properties of the protein released into the oral cavity when one chews the tablet causing it to be disintegrated. Saliva and particles of food entrapped within the mouth are absorbed and carried into the stomach when the tablet is digested.

The odor causing particles or materials are then deodorized within the stomach by the action of the Yucca extract. Gasses subsequently ensuing from the stomach during the normal course of breathing and talking will exhibit a pleasant smell.

The Yucca extract utilized in this invention is obtained from Ritter International Company of Los Angeles, Calif. and is sold under the trade names Yucca Foam and Yucca Roam. It is a concentrated natural extract of *Yucca Brevifolia* or *Yucca Schidigera*. It characteristically comes as a 50% solid.

The protein Soya Isolate or Isolated Soya Protein has been shown to be an effective scavenger for cleansing the mouth by picking up or absorbing all of the moisture and odor producing particles that may be present and carrying them to the stomach upon swallowing. Any type of food grade vegetable protein such as cornmeal, oatmeal, wheat germ, and other vegetable material would be satisfactory.

The desired effect is achieved by the combined action of the two active ingredients discussed above. However, in order to provide these ingredients to the user in a palatable and useful form, these ingredients are compounded with fillers, sweeteners, and coloring agents along with other materials required to form tablets, liquids, gums or sprays.

The preferred tablet composition contains 12.00% Yucca extract, which reduces to 6.76% when dried to approximately 3% moisture content; 15.00% of a sweetener such as sucrose or sodium saccharin; 56.24% Soya Isolate (profam 90/ls); 1.0% water soluble chlorophyll as a coloring agent; 0.5% Magnesium Stearate as a lubricant; 10.0% Glyceryl Mono Stearate (Atmos 150) as an excipient; 10.0% micro crystalline cellulose (Avicel) as a binder; and 0.5% of redistilled Oleum Menthae Piperitae (Peppermint Oil) as a flavoring agent.

Other composition may be prepared with; from 1 to 90% of the dried Yucca extract (3% moisture), from 0.5% to 50% of the sweetener, from 10.0 to 90.0% of a protein having scavenging or absorptive characteristics, from 0.2 to 3% of magnesium stearate or a lubricant such as calcium stearate, zinc stearate or other standard lubricants, from 1 to 15% each of Atmos 150 and Avicel, from 0.01 to 10% of chlorophyll or another coloring agent selected from vegetable dyes or other well known food grade dyes, and from 0.05 to 30% of Peppermint Oil or another flavoring agent such as Wintergreen Oil, Oil of Spearmint, Orange Oil and Lemon Oil.

In practice, the Yucca extract which normally comes as a 50% solids extract (50% solids and 50% water by weight) is blended with the sweetener, coloring agent, flavoring agent and protein. Water is added to obtain a mixture that will granulate.

After the blending has been completed, the mixture is placed onto trays and dried to approximately 3% moisture content by placing it into an oven set at temperatures ranging from 120 to 180° F. for approximately 48 hours.

The dried mixture is then placed into a mill and pulverized.

The binding agent, flavoring agent, excipient and lubricant is then added to the dried pulverized mixture and blended thoroughly. This material is then suitable for compression in a tablet machine.

Tablets containing approximately 630 mg of the preferred composition were tested and found to be extremely effective in eliminating or reducing odors from liquor, tabacco, garlic, and onions, as well as denture and natural breath odors. However, tablets containing as little as 5 mg of the preferred composition also proved to be effective in most instances.

The active ingredients of this invention may be compounded into sprays, gums and/or liquids with equally effective results. The key to the elimination of oral cavity odors is to first purge the odor producing substances from the oral cavity and then deoderize them. By utilizing a purging agent which enters the digestive system and is slow to enter the blood stream, the non-deodorized materials are passed through the body or transformed by digestive processes. The Yucca extract deodorizes the major portion of the absorbed materials in the oral cavity and stomach before the odors accompanying the digested materials enter the blood stream.

Having fully disclosed my invention as well as how to make and use it, the scope of my claims may be understood as follows.

I claim:

1. A breath deodorizing composition comprising from 1.0–90.0% by weight of the 50% solids extract from the *Yucca Brevifolia* or *Schidigera* plant, dried to approximately 3% moisture content, blended with from 10.0 to 90.0% of a food grade vegetable protein.

2. The composition of claim 1 wherein said protein is selected from the group consisting of Soya Isolate, cornmeal, oatmeal and wheat germ.

3. A breath deodorizing tablet capable of effectively reducing or eliminating tobacco and alcoholic odors from the oral cavity comprising from 1.0–90.0% by weight of the 50% solids extract from the *Yucca Brevifolia* or *Schidigera* plant, dried to approximately 3% moisture content, blended with from 10.0 to 90.0% of a food grade vegetable protein.

4. The tablet of claim 3 comprising a sweetener, a coloring agent selected from vegetable dyes or other food grade dyes, a lubricant, an excipient, a binder, and a flavoring agent blended with said extract and protein wherein said protein is soya isolate.

5. The tablet of claim 4 wherein said sweetener is sucrose, said coloring agent is a water soluble chlorophyll, said excipient is Atmos 150, said binder is Avicel, said lubricant is selected from the group consisting of magnesium-, zinc- and calcium-stearate and said flavoring agent is selected from the group consisting of peppermint oil, wintergreen oil, oil of spearmint, orange oil and lemon oil.

6. The tablet of claim 5 wherein said lubricant is magnesium stearate and said flavoring agent is peppermint oil.

7. The tablet of claim 5 wherein said sucrose is replaced by sodium saccharin.

* * * * *